United States Patent [19]

Hemmerle

[11] Patent Number: 5,608,086

[45] Date of Patent: Mar. 4, 1997

[54] PROCESS FOR THE PREPARATION OF INTERMEDIATES FOR THE SYNTHESIS OF GLUCOSE-6-PHOSPHATASE INHIBITORS, AND NOVEL INTERMEDIATES

[75] Inventor: Horst Hemmerle, Lorsch, Germany

[73] Assignee: Hoechst Aktiengesellschaft, Frankfurt am Main, Germany

[21] Appl. No.: 421,974

[22] Filed: Apr. 14, 1995

[30] Foreign Application Priority Data

Apr. 18, 1994 [DE] Germany .................... 44 13 402.9

[51] Int. Cl.$^6$ .................................... C07D 317/72
[52] U.S. Cl. ........................................ 549/336
[58] Field of Search ............................. 549/336

[56] References Cited

FOREIGN PATENT DOCUMENTS 2105709 3/1994 Canada .
587088 3/1994 European Pat. Off. .

*Primary Examiner*—C. Warren Ivy
*Assistant Examiner*—Amelia Owens
*Attorney, Agent, or Firm*—Finnegan, Henderson, Farabow, Garrett & Dunner, L.L.P.

[57] ABSTRACT

Cyclohexane derivatives of the formula I

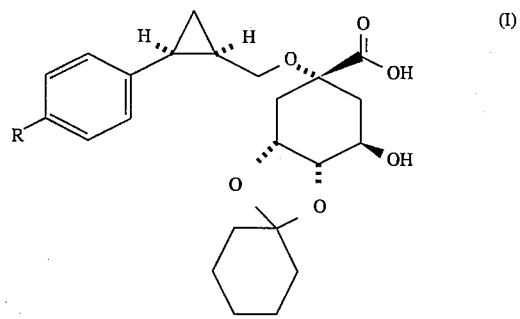

in which the radicals are as defined in the description, and processes for the preparation of these compounds, are described. Also described are novel intermediates for the preparation of the compounds of the formula I.

4 Claims, No Drawings

PROCESS FOR THE PREPARATION OF INTERMEDIATES FOR THE SYNTHESIS OF GLUCOSE-6-PHOSPHATASE INHIBITORS, AND NOVEL INTERMEDIATES

DESCRIPTION

EP-A-0 587 088 relates to substituted cyclohexane derivatives which inhibit the glucose-6-phosphatase system of the liver. The compounds are therefore suitable for the treatment of diseases which are connected with increased activity of the glucose-6-phosphatase system. The cyclohexane derivatives of EP-A-0 587 088 have a number of stereocenters.

A process has now been found which enables certain cyclohexane derivatives of EP-A-0 587 088 to be prepared in enantiomerically pure form.

The invention accordingly relates to a process for the preparation of a compound of the formula I

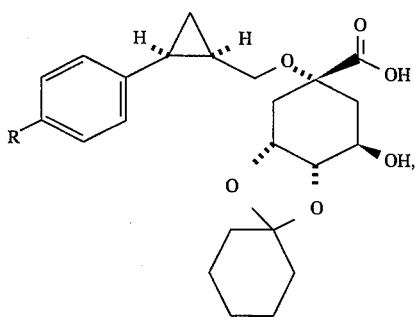
(I)

in which R is fluorine, chlorine or methyl, which comprises opening the lactone ring of 1,2-O-cyclohexylidene-3,5-lactonylcyclohexane-1,2-diol of the formula 1

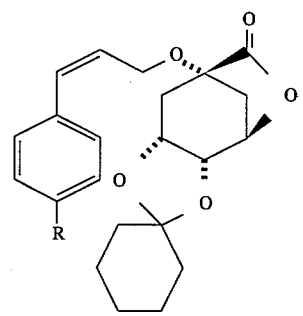
(1)

by base catalysis to form an alcohol of the formula 2

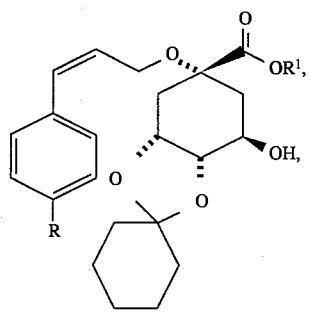
(2)

in which R is as defined for formula I and $R^1$ is $C_1-C_{10}$-alkyl (straight-chain or branched) or benzyl, reacting the resulting alcohol of the formula 2 with an acid chloride in the presence of a base to give an ester of the formula 3

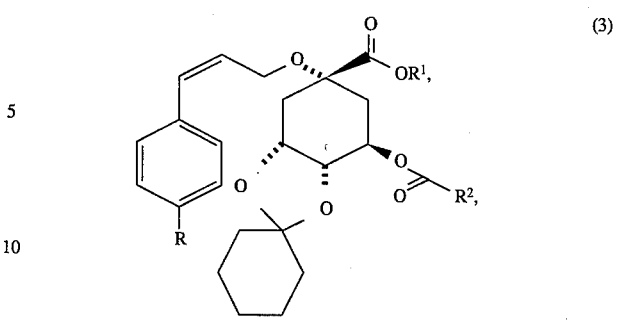
(3)

in which R is as defined for formula I and $R^1$ is as defined for formula 2, and $R^2$ is $C_1-C_{10}$-alkyl (straight-chain or branched), phenyl or naphthyl, and reacting a resulting compound of the formula 3 with a carbene to give a diastereomer mixture of the cyclopropyl derivatives of the formulae 4A and 4B

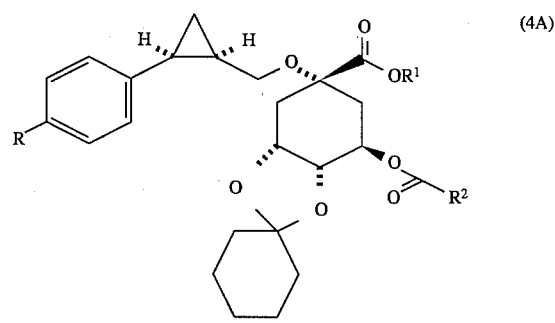
(4A)

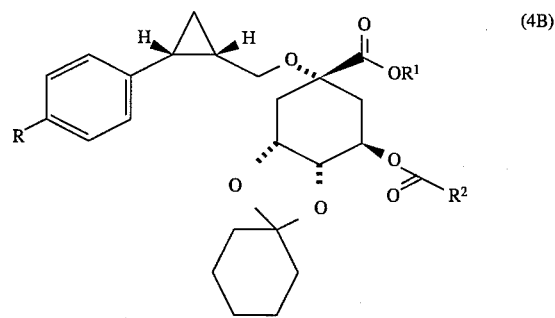
(4B)

in which R, $R^1$ and $R^2$ are as defined for the formulae I, 2 and 3, in which 4A is present in a distinct excess, isolating a compound of the formula 4A from the mixture by crystallization and converting it into a compound of the formula I by alkaline hydrolysis followed by acidification.

The process is preferably carried out as follows:

In the first step, the lactone ring of the lactone 1 (cf. EP-A-0 587 088, Example 68A) is opened by base catalysis in an alcohol (a $C_1-C_{10}$ alkanol or benzyl alcohol) at from 0° C. to the boiling point of the solvent, to give 2 (the preferred temperature range is 0°–25° C.). In order to increase the solubility of 1 it is possible to add inert solvents such as tetrahydrofuran or dioxane. The base used is the alkali metal alcoholate of the alcohol with which it is intended to open the lactone 1 to give 2; the sodium or potassium alcholates are preferred.

In the 2nd step the alcohol 2 is reacted with an acid chloride ($r^2$ is preferably $C_1-C_{10}$-alkyl or phenyl) in an inert aprotic solvent, preferably dichloromethane, at from −20° C. to the boiling point of the solvent in the presence of a base such as triethylamine, ethyldiisopropylamine or pyridine and, in addition, dimethylaminopyridine—triethylamine is preferred—to give 3.

In the 3rd step the alkene (ester) 3 is dissolved in an inert solvent such as dichloroethane, dichloromethane or toluene and the solution is added at from −20° to −40° C. to a reagent solution of diiodomethane/diethyl zinc or chloroiodomethane/diethyl zinc in an inert solvent which has been indicated above. A mixture of 4A and 4B is obtained in which 4A is present in a distinct excess (4A:4B about 5:1). 4A can be obtained with a diastereomeric purity>98% by conventional crystallization.

In the 4th step, by means of alkaline hydrolysis followed by acidification with acid such as hydrochloric acid or acetic acid, 4A gives the compound of the formula I.

The advantage over the process described in EP-A-0 587 088 consists in the reversal of the diastereomeric proportions of the cyclopropyl side chain. Whereas in the process of EP-A-0 587 088 the 1S,2R-cyclopropane 5A (R=chlorine) is formed with a selectivity of about 4:1

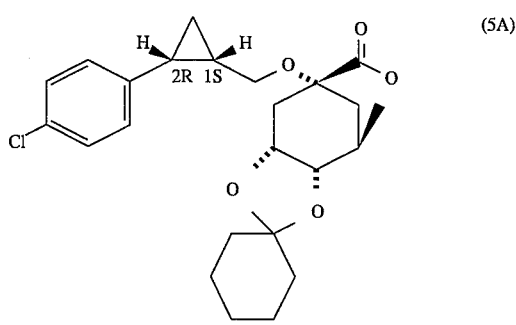

(5A)

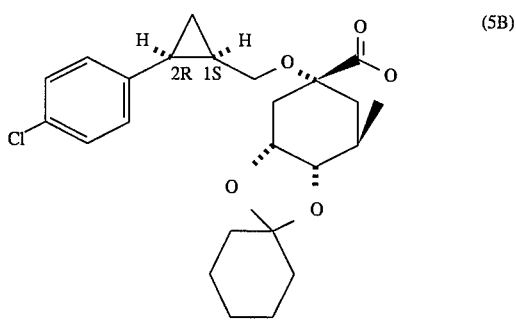

(5B)

in the process of the invention 4A and 4B are obtained with a selectivity of 5:1.

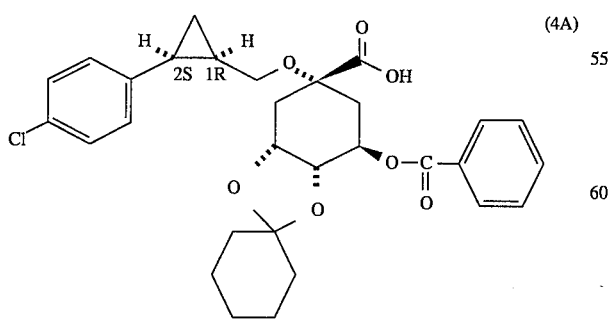

(4A)

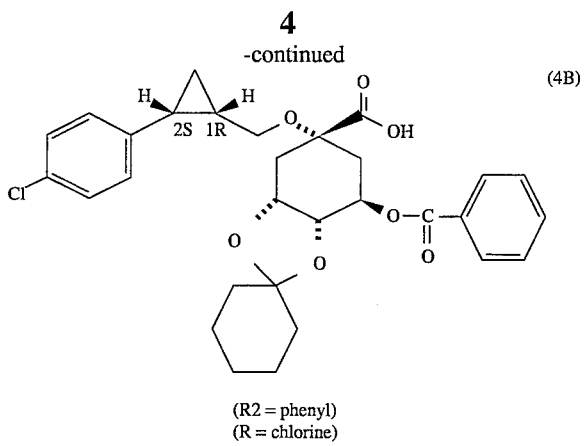

(4B)

(R2 = phenyl)
(R = chlorine)

The compound of the formula I is a valuable intermediate for the preparation of glucose-6-phosphatase inhibitors in accordance with EP-A-0 587 088. The further reaction of compound I to give the cyclohexane derivatives according to EP-A-0 587 088 is carried out, for example, in analogy to the method A described in said document.

The glucose-6-phosphatase inhibitors which can be obtained from compound I are approximately 10 times more active than the inhibitors prepared from compound 5A. Using the compound I it has become possible for the first time to prepare the more effective diastereomer of a compound of EP-A-0 587 088 in a diastereo-selective manner.

The compounds I and the compounds 2, 3 and 4A were not described in EP-A-0 587 088. The invention relates accordingly to these compounds too. They all represent valuable intermediates for the synthesis of cyclohexane derivatives, for example in accordance with EP-A-0 587 088.

EXAMPLE 1

Stage 1:

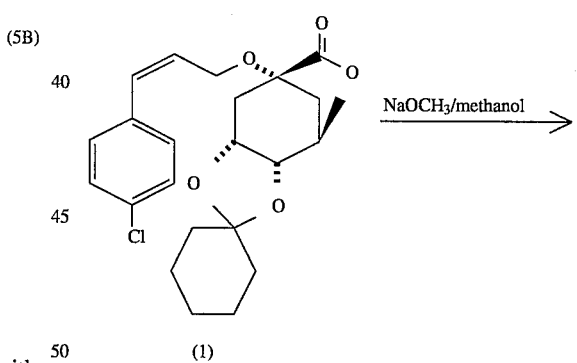

(1)

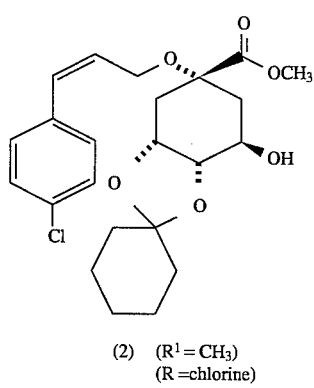

(2)  ($R^1 = CH_3$)
    (R = chlorine)

2.95 g (0.0985 mol) of 80% pure NaH were added in portions at room temperature under an argon atmosphere to a solution of 5 l of anhydrous methanol and 1.5 l of anhydrous tetrahydrofuran. Subsequently, compound 1 (cf. EP-A-0 587 088) was added as a solid, likewise at room temperature. After 3–4 hours a clear solution was obtained. This solution was worked up by adding 6.0 g of glacial acetic acid (pH≅5) followed by 2 l of water in portions. A fluffy precipitate of unreacted lactone was formed which could be filtered off without problems (recovery of starting material!).

The filtrate was subsequently concentrated until a thick white precipitate had formed. The mixture was cooled with ice and the precipitate was filtered off with suction and washed with ice-cold methanol/water 1:1.

The precipitate was dried at 1 mbar and 40° C. to give 370 g (86%) of compound 2 as a colorless solid.
m.p.: 102°–104° C.
Stage 2:

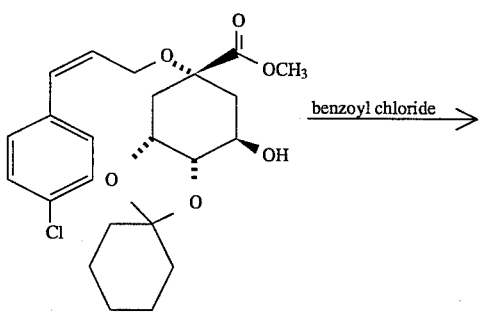

(2)  (R$^1$ = CH$_3$)
     (R = chlorine)

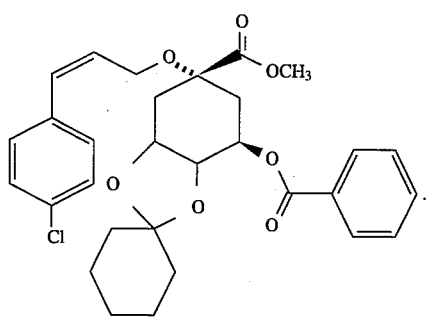

(3)  (R$^1$ = CH$_3$, R$^2$ = phenyl)
     (R = chlorine)

384.0 g (0.879 mol) of the alcohol 2 from stage 1 were dissolved in 1.3 l of anhydrous dichloromethane. Subsequently, 10.74 g (0.0879 mol) of 4-dimethylaminopyridine and 364.8 ml (2,637 mol) of anhydrous triethylamine were added. The solution was cooled to 0°–10° C. and a solution of 164.7 ml (1.418 mol) of benzoyl chloride in 350 ml of anhydrous dichloromethane was added dropwise. After 4 hours at room temperature only traces of starting material were still present. TLC: ethyl acetate/cyclohexane 1:2

The reaction product was poured into 1.5 l of water/400 g of Na$_4$Cl/1 l of ice. It was then extracted twice with dichloromethane and washed once with saturated bicarbonate solution, and the combined organic phases were dried over Na$_2$SO$_4$. After concentration the residue was crystallized from isopropanol. 437.0 g (91.9%) of product 3 were obtained.
m.p.: 104°–107° C.
Stage 3:

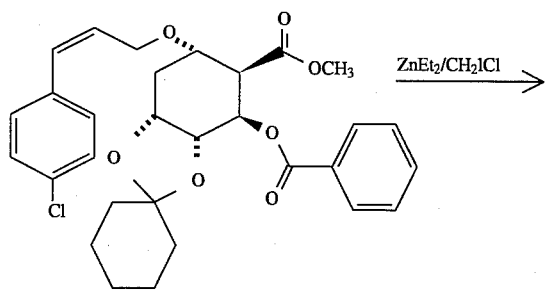

(3)  (R$^1$ = CH$_3$, R$^2$ phenyl, R = chlorine)

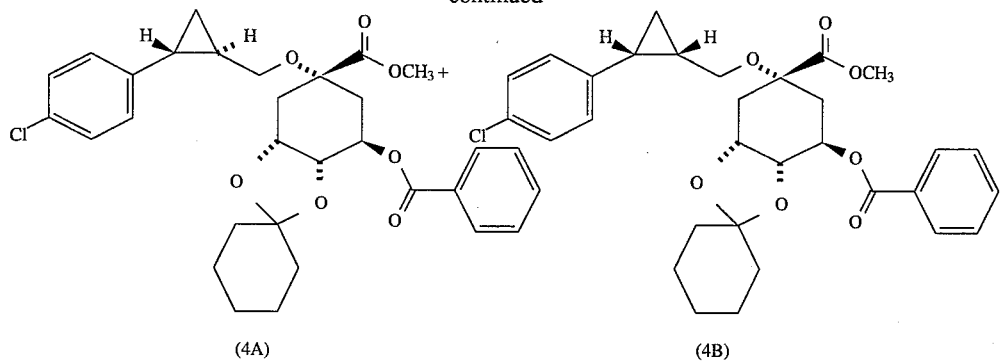

(4A)

($R^1 = CH_3$, $R^2$ = phenyl, R = Chlorine)

(4B)

After crystalization  5:1
>98:<2

80.5 ml (0.785 mol) of pure diethyl zinc were transferred under pressure from a steel bomb, using a steel canula, into 2 l of anhydrous dichloroethane ** at 0° C. under an argon atmosphere.

** instead of dichloroethane, other inert solvents have also been used (dichloromethane, toluene, THF).

Stage 4:

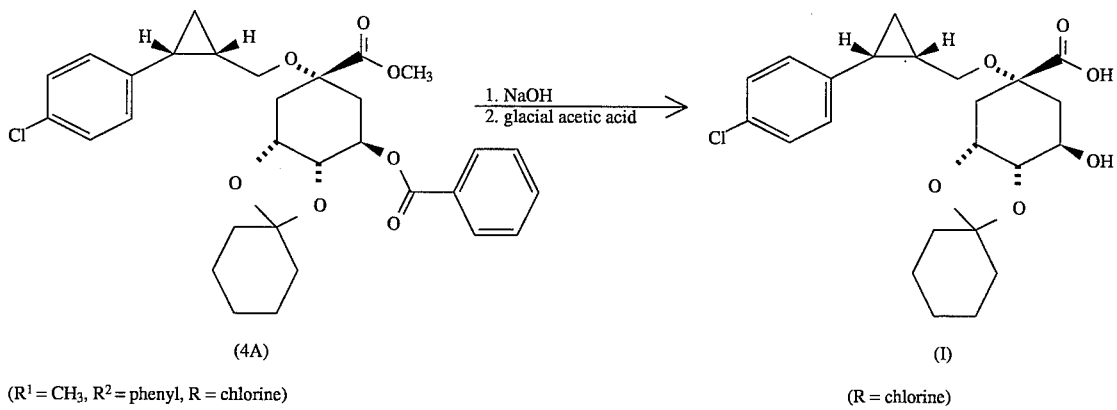

(4A)

($R^1 = CH_3$, $R^2$ = phenyl, R = chlorine)

(I)

(R = chlorine)

Subsequently, 114.4 ml (1.57 mol) of chloroiodomethane were added dropwise at 0°–10° C., the resulting suspension was stirred for 30 minutes and then 169.89 g (0.314 mol) of the olefin 3 from stage 2 dissolved in 500 ml of anhydrous dichloroethane were added dropwise. After hour at 0°–10° C. the reaction mixture was allowed to heat up to room temperature and was stirred for a further hours at room temperature. Under a nitrogen atmosphere, the reaction mixture was poured slowly into a solution of 300 g of $NH_4Cl/1.5$ l of ice-water and was extracted with dichloromethane. The combined organic phases were extracted by shaking with saturated NaCl solution and dried over $Na_2SO_4$.

The majority of the solvent was subsequently removed by concentration in vacuo and the remaining mixture was diluted with isopropanol. The diluted mixture was then concentrated further until a thick precipitate was formed. This precipitate was filtered off with suction and recrystallized twice from isopropanol to give 109.8 g (63%) of compound 4A with a diastereomeric excess>98%.

m.p.: 143°–144° C.

* instead of pure diethyl zinc it is also possible to use a 1 molar solution in toluene (Aldrich).

99.0 g (0.178 mol) of the compound 4A from stage 3 were dissolved in 1200 ml of dioxane, and 890 ml of 2N sodium hydroxide solution were added. The suspension was heated at 80° C. for 2 hours.

The reaction solution was cooled to about 10° C. and 228 ml (2 mol) of half-concentrated glacial acetic acid were slowly added dropwise (pH 5–6). The solution was then concentrated on a rotary evaporator until the first signs of clouding appeared. The resulting concentrate was poured with vigorous stirring into about 1500 ml of water, from which after stirring for 10 minutes a crystalline precipitate was formed. This precipitate was filtered off with suction and dried in vacuo at 22° C. under 0.5 bar.

82.2 g of a compound I where R=chlorine were obtained.

EXAMPLE 2

Working analogously to Example 1 gives the compound of the formula

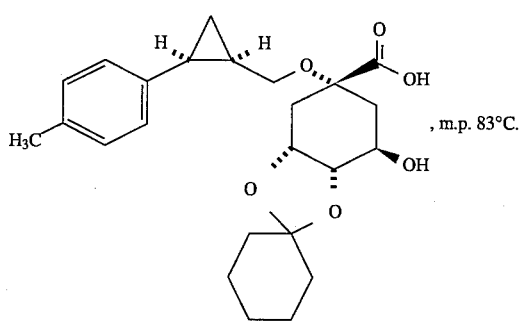, m.p. 83°C.

EXAMPLE 3

Working analogously to Example 1 gives the compound of the formula

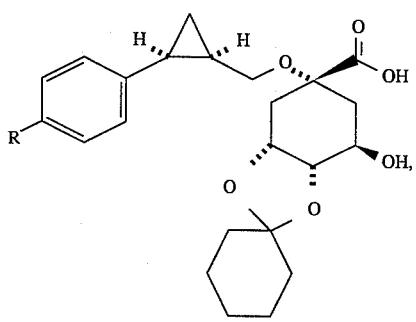

m/z=427 (M+H⁺)

I claim:

1. A process for the preparation of a compound of the formula I

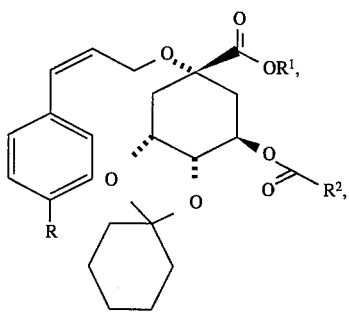 (I)

in which R is fluorine, chlorine or methyl, which comprises opening the lactone ring of 1,2-O-cyclohexylidene-3,5-lactonylcyclohexane-1,2-diol of the formula 1

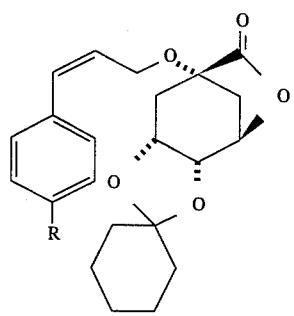 (1)

by base catalysis to form an alcohol of the formula 2

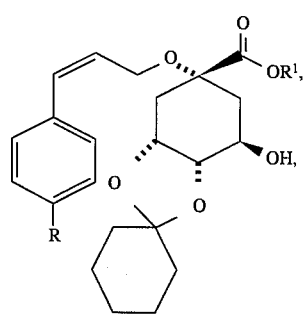 (2)

in which R is as defined for formula I and $R^1$ is a straight-chain or branched $C_1$–$C_{10}$-alkyl or benzyl, reacting a resulting alcohol of the formula 2 with an acid chloride in the presence of a base to give an ester of the formula 3

(3)

in which R is as defined for formula I and $R^1$ is as defined for formula 2, and $R^2$ is a straight-chain or branched $C_1$–$C_{10}$-alkyl, phenyl or naphthyl, and reacting the resulting compound of the formula 3 with a carbene to give a diastereomer mixture of the cyclopropyl derivatives of the formulae 4A and 4B

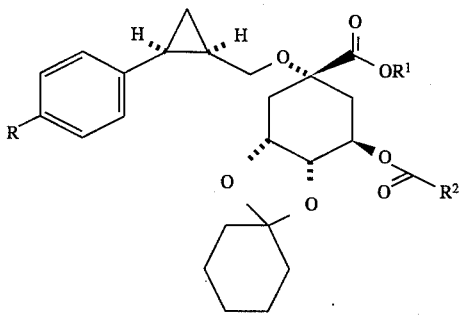 (4A)

11
-continued

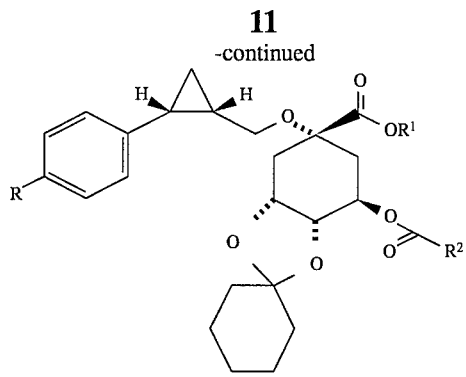
(4B)

in which R, $R^1$ and $R^2$ are as defined for the formulae I, 2 and 3, in which 4A is present in a distinct excess, isolating a compound of the formula 4A from the mixture by crystallization and converting it into a compound of the formula I by alkaline hydrolysis followed by acidification.

2. A compound of the formula I

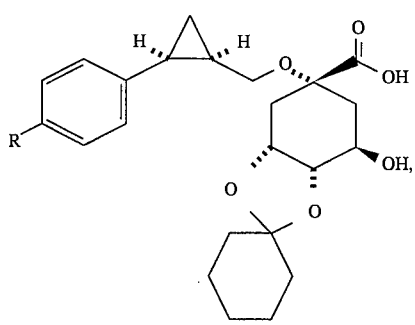
(I)

in which R is fluorine, chlorine or methyl.

3. An alcohol of the formula 2

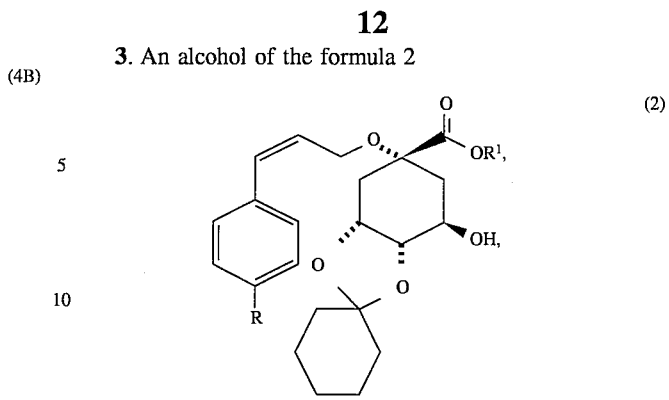
(2)

in which R is fluorine, chlorine or methyl and $R^1$ is a straight-chain or branched $C_1$–$C_{10}$-alkyl or benzyl.

4. A cyclopropyl derivative of the formula 4A

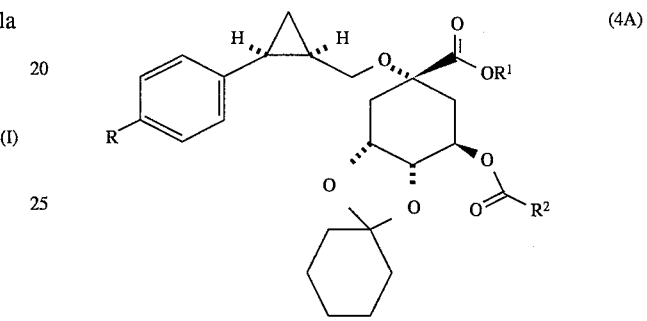
(4A)

in which R is fluorine, chlorine or methyl, $R^1$ is $C_1$–$C_{10}$-alkyl (straight-chain or branched) or benzyl, and $R^2$ is $C_1$–$C_{10}$-alkyl (straight-chain or branched) phenyl or naphthyl.

* * * * *